United States Patent [19]

Berg

[11] Patent Number: 4,729,818

[45] Date of Patent: Mar. 8, 1988

[54] DEHYDRATION OF ACETIC ACID BY EXTRACTIVE DISTILLATION

[76] Inventor: Lloyd Berg, 1314 S. Third Ave., Bozeman, Minn. 59715

[21] Appl. No.: 38,966

[22] Filed: Apr. 16, 1987

[51] Int. Cl.$^4$ .......................... B01D 3/40; C07C 51/44; C07C 53/08

[52] U.S. Cl. .......................... 203/16; 203/51; 203/57; 203/58; 203/60; 203/61; 203/62; 562/608

[58] Field of Search .................. 203/16, 61, 51, 60, 203/62, 64, 57, 58; 562/608

[56] References Cited

U.S. PATENT DOCUMENTS

| | | | |
|---|---|---|---|
| 1,477,076 | 12/1923 | Piron | 203/16 |
| 1,996,755 | 4/1935 | Dreyfus | 203/51 |
| 2,041,668 | 5/1903 | Wentworth | 203/16 |
| 2,588,268 | 3/1952 | Mercer et al. | 203/16 |
| 2,651,605 | 9/1953 | Hartley et al. | 203/60 |
| 3,951,755 | 4/1976 | Sartorius et al. | 203/60 |
| 4,353,784 | 10/1982 | Koga et al. | 562/608 |

FOREIGN PATENT DOCUMENTS

| | | | |
|---|---|---|---|
| 39-12915 | 7/1964 | Japan | 562/608 |
| 445645 | 12/1974 | U.S.S.R. | 203/61 |

*Primary Examiner*—Wilbur Bascomb

[57] ABSTRACT

Acetic acid cannot be easily removed from acetic acid—water mixtures by distillation because of the closeness of their boiling points and the deviation from ideal solution behavior. Acetic acid can be readily removed from mixtures containing it and water by using extractive distillation in which the extractive distillation agent is a mono carboxylic acid, either singly or admixed with high boiling organic compounds. Typical examples of effective agents are pelargonic acid; heptanoic acid and isophorone; neodecanoic acid, acetophenone and nitrobenzene.

1 Claim, No Drawings

DEHYDRATION OF ACETIC ACID BY EXTRACTIVE DISTILLATION

FIELD OF THE INVENTION

This invention relates to a method for dehydrating acetic acid using certain higher boiling liquids as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boils twenty Centrigrade degrees or more than the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

Currently there are at least four commercial ways to manufacture acetic acid. The fermentation of fruit (apples) or wood waste are the oldest. The reaction of acetylene with water to form acetaldehyde followed by air oxidation is still in use. Fermentation of ethanol to acetic acid is used when cheap ethanol is available. The reaction of methanol with carbon monoxide in aqueous solution is currently in favor because of cheap methanol. The air oxidation of butane to give a multitude of products, approximately forty, including acetic acid is currently attractive. All of these processes present the problem of separating water from acetic acid. Acetic acid boils at 118° C., water at 100° C. but although these two do not form an azeotrope, they are from being an ideal mixture. The separation of water from acetic acid by distillation becomes especially difficult at high concentrations of acetic acid. Currently they are separated by azeotropic distillation. In this process, the azeotrope former is a compound such as butyl acetate which takes the water off overhead as a two-phase azeotrope. The water is decanted and the butyl acetate recycled. Many azeotrope forming compounds have been suggested for this separation. Anything that forms a two-phase azeotrope with water, e.g. is insoluble in water, is soluble in acetic acid but does not form an azeotrope with acetic acid, will accomplish this mode of separation.

Extractive distillation would be an attractive method of effecting the separation of acetic acid from water if agents can be found that (1) will create a large apparent relative volatility between water and acetic acid and (2) are easy to recover from acetic acid, that is, form no azeotrope with acetic acid and boil sufficiently above acetic acid to make the separation by rectification possible with only a few theoretical plates.

Extractive distillation typically requires the addition of an equal amount to twice as much extractive agent as the acetic acid—water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents requires if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with acetic acid otherwise it will form a two-phase azeotrope with acetic acid in the recovery column and some other method of separation will have to be employed.

R. Sartorius & H. Stapf, U.S. Pat. No. 3,951,755, Apr. 20, 1976 described an extractive distillation process to dehydrate acetic acid using N-methyl acetamide.

OBJECTIVE OF THE INVENTION

The object of this invention is to provide a process or method of extractive distillation that will enhance the relative volatility of water from acetic acid in their separation in a rectification column. It is a further object of this invention too identify organic compounds which in addition to the above constraints, are stable, can be separated from acetic acid by rectification with relatively few theoretical plates and can be recycled to the extractive distillation column and reused with little decomposition.

TABLE 1

| Extractive Agents | Ratio | | Relative Volatility Not Normalized | |
|---|---|---|---|---|
| None, 80% Acetic acid | | | 2.0 | |
| None, 90% Acetic acid | | | 1.9 | |
| Benzoic acid | 1 | 6/5 | 2.5 | 5.8 |
| Benzoic acid, Butyl benzoate | $(1/2)^2$ | $(3/5)^2$ | 5.8 | 4.3 |
| Benzoic acid, Dimethylformamide | " | " | 5.1 | 3.1 |
| Benzoic acid, N,N—Dimethylacetamide | " | " | 7.8 | 7.9 |
| Benzoic acid, Methyl salicylate | " | " | 5.0 | 5.2 |
| Benzoic acid, Acetamide, Dimethylformamide | $(1/3)^3$ | $(2/5)^3$ | 5.7 | 8.7 |
| Benzoic acid, Acetophenone, Cinnamic acid | " | " | 5.3 | 5.4 |
| Benzoic acid, Acetophenone, Butyl benzoate | " | " | 5.1 | 4.8 |
| Benzoic acid, Acetophenone, Salicylic acid | " | " | 6.1 | 6.9 |

*Effective Extractive Distillation Agents*

TABLE 1-continued

Effective Extractive Distillation Agents

| Extractive Agents | Ratio | | Relative Volatility Not Normalized | |
|---|---|---|---|---|
| Benzoic acid, Adiponitrile, Cinnamic acid | " | " | 4.4 | 4.5 |
| Benzoic acid, Adiponitrile, Salicylic acid | " | " | 4.3 | 5.1 |
| Benzoic acid, Methyl salicylate, Salicylic acid | " | " | 5.4 | 4.1 |
| Benzoic acid, Methyl salicylate, Succinic acid | " | " | 5.6 | 4.2 |
| Benzoic acid, N,N—Dimethylacetamide, Salicylic acid | " | " | 5.8 | 5.0 |
| Cinnamic acid, Acetophenone | $(1/2)^2$ | $(3/5)^2$ | 7.3 | 6.5 |
| Cinnamic acid, Adiponitrile | " | " | 4.3 | 6.4 |
| Cinnamic acid, Methyl salicylate | " | " | 4.0 | 4.5 |
| Cinnamic acid, Acetophenone, Benzophenone | $(1/3)^3$ | $(2/5)^3$ | 6.8 | 4.9 |
| Hexanoic acid | 1 | 6/5 | 5.4 | 6.5 |
| Hexanoic acid, Acetophenone | $(1/2)^2$ | $(3/5)^2$ | 5.4 | 6.2 |
| Hexanoic acid, Decanoic acid | " | " | 4.1 | 4.7 |
| Hexanoic acid, Dipropylene glycol dibenzoate | " | " | 5.1 | 4.7 |
| Hexanoic acid, Ethylene glycol diacetate | " | " | 4.7 | 5.5 |
| Hexanoic acid, Heptanoic acid | " | " | 5.6 | 4.5 |
| Hexanoic acid, Isophorone | " | " | 5.1 | 6.7 |
| Hexanoic acid, Methyl n-amyl ketone | " | " | 6.2 | 7.8 |
| Hexanoic acid, Methyl benzoate | " | " | 5.0 | 5.6 |
| Hexanoic acid, Neodecanoic acid | " | " | 5.6 | 5.8 |
| Hexanoic acid, Nitrobenzene | " | " | 7.9 | 9.0 |
| Hexanoic acid, 3-Nitrotoluene | " | " | 6.1 | 6.5 |
| Hexanoic acid, Octanoic acid | " | " | 5.1 | 3.8 |
| Hexanoic acid, Octanoic - Decanoic acids | " | " | 4.7 | 5.1 |
| Hexanoic acid, Pelargonic acid | " | " | 5.4 | 5.9 |
| Hexanoic acid, Acetophenone, Benzoic acid | $(1/3)^3$ | $(2/5^3)$ | 3.6 | 5.0 |
| Hexanoic acid, Acetophenone, Methyl n-amyl ketone | " | " | 7.0 | 7.1 |
| Hexanoic acid, Acetophenone, Glutaric acid | " | " | 5.3 | 5.3 |
| Hexanoic acid, Acetophenone, Methyl benzoate | " | " | 4.9 | 5.7 |
| Hexanoic acid, Acetophenone, Decanoic acid | " | " | 4.5 | 4.9 |
| Hexanoic acid, Acetophenone, Nitrobenzene | " | " | 5.1 | 6.4 |
| Hexanoic acid, Acetophenone, 3-Nitrotoluene | " | " | 5.5 | 5.4 |
| Hexanoic acid, Acetophenone, Pelargonic acid | " | " | 6.8 | 6.8 |
| Hexanoic acid, Decanoic acid, Isophorone | " | " | 5.4 | 6.4 |
| Hexanoic acid, Octanoic acid, Methyl benzoate | " | " | 4.3 | 4.6 |
| Hexanoic acid, Pelargonic acid, Et glycol diacetate | " | " | 5.2 | 4.5 |
| Hexanoic acid, Octanoic acid, Me salicylate | " | " | 5.6 | 4.5 |
| Heptanoic acid | 1 | 6/5 | 5.2 | 5.5 |
| Heptanoic acid, Decanoic acid | $(1/2)^2$ | $(3/5)^2$ | 5.0 | 5.2 |
| Heptanoic acid, Dipropylene glycol dibenzoate | " | " | 4.8 | 4.8 |
| Heptanoic acid, Ethylene glycol diacetate | " | " | 4.7 | 5.8 |
| Heptanoic acid, Isophorone | " | " | 5.2 | 6.4 |
| Heptanoic acid, Methyl n-amyl ketone | " | " | 4.9 | 5.5 |
| Heptanoic acid, Nitrobenzene | " | " | 6.5 | 5.6 |
| Heptanoic acid, Octanoic acid | " | " | 5.1 | 5.6 |
| Heptanoic acid, Octanoic - Decanoic acids | " | " | 5.0 | 4.2 |
| Heptanoic acid, Pelargonic acid | " | " | 6.9 | 6.4 |
| Heptanoic acid, Acetophenone, Decanoic acid | $(1/3)^3$ | $(2/5)^3$ | 4.8 | 4.3 |
| Heptanoic acid, Acetophenone, Dipropylene glycol dibenzoate | " | " | 6.1 | 5.8 |
| Heptanoic acid, Acetophenone, Nitrobenzene | " | " | 4.8 | 4.9 |
| Heptanoic acid, Acetophenone, Methyl n-amyl ketone | " | " | 6.0 | 5.4 |
| Heptanoic acid, Acetophenone, Octanoic acid | " | " | 5.2 | 5.0 |
| Heptanoic acid, Acetophenone, Octanoic-Decanoic acids | " | " | 4.6 | 6.6 |
| Heptanoic acid, Acetophenone, Pelargonic acid | " | " | 4.9 | 4.4 |
| Heptanoic acid, Decanoic acid, Methyl benzoate | " | " | 6.0 | 4.7 |
| Heptanoic acid, Decanoic acid, Isophorone | " | " | 7.5 | 5.7 |
| Heptanoic acid, Ethylene glycol diacetate, Neodecanoic acid | " | " | 4.9 | 4.0 |
| Heptanoic acid, Ethylene glycol diacetate, Octa-Deca acids | " | " | 4.1 | 6.6 |
| Heptanoic acid, Ethylene glycol, Pelargonic acid | " | " | 4.9 | 4.8 |
| Heptanoic acid, Pelargonic acid, Isophorone | " | " | 7.6 | 7.6 |
| Heptanoic acid, Pelargonic acid, Methyl isoamyl ketone | " | " | 5.8 | 6.3 |
| Heptanoic acid, Pelargonic acid, Methyl benzoate | " | " | 5.2 | 4.0 |
| Octanoic acid | 1 | 6/5 | 4.1 | 4.8 |
| Octanoic acid, Acetophenone | $(1/2)^2$ | $(3/5)^2$ | 5.6 | 5.6 |
| Octanoic acid, Decanoic acid | " | " | 4.4 | 6.2 |
| Octanoic acid, Dipropylene glycol dibenzoate | " | " | 6.1 | 6.8 |
| Octanoic acid, Ethylene glycol diacetate | " | " | 4.0 | 4.7 |
| Octanoic acid, Isophorone | " | " | 5.5 | 4.8 |
| Octanoic acid, Methyl n-amyl ketone | " | " | 6.2 | 6.5 |
| Octanoic acid, Methyl benzoate | " | ' | 5.3 | 7.0 |
| Octanoic acid, Methyl salicylate | " | " | 4.8 | 5.5 |
| Octanoic acid, Neodecanoic acid | " | " | 5.9 | 6.1 |
| Octanoic acid, Nitrobenzene | " | " | 4.9 | 4.6 |
| Octanoic acid, 3-Nitrotoluene | " | " | 6.4 | 6.9 |
| Octanoic acid, Pelargonic acid | " | " | 4.7 | 5.5 |
| Octanoic acid, Acetophenone, Methyl n-amyl Ketone | $(1/3)^3$ | $(2/5)^3$ | 6.7 | 6.7 |
| Octanoic acid, Acetophenone, Decanoic acid | " | " | 5.8 | 5.4 |
| Octanoic acid, Acetophenone, Nitrobenzene | " | " | 4.6 | 5.4 |
| Octanoic acid, Acetophenone, 3-Nitrotoluene | " | " | 5.7 | 5.0 |
| Octanoic acid, Acetophenone, Pelargonic acid | " | " | 5.9 | 6.4 |

TABLE 1-continued
Effective Extractive Distillation Agents

| Extractive Agents | Ratio | | Relative Volatility Not Normalized | |
|---|---|---|---|---|
| Octanoic acid, Benzyl benzoate, Neodecanoic acid | " | " | 5.0 | 4.5 |
| Octanoic acid, Decanoic acid, Isophorone | " | " | 4.4 | 4.9 |
| Octanoic acid, Decanoic acid, Methyl benzoate | " | " | 4.6 | 4.7 |
| Octanoic acid, Pelargonic acid, Ethylene glycol diacetate | " | " | 7.1 | 7.0 |
| Octanoic acid, Pelargonic acid, Isophorone | " | " | 5.1 | 4.8 |
| Octanoic acid, Pelargonic acid, Methyl benzoate | " | " | 8.2 | 6.3 |
| Octanoic acid, Pelargonic acid, Methyl salicylate | " | " | 5.1 | 5.6 |
| Octanoic acid, Dipropylene glycol dibenzoate, Ethylene glycol diacetate | " | " | 5.8 | 6.2 |
| Octanoic - Decanoic acids, Cinnamic acid | $(1/2)^2$ | $(3/5)^2$ | 4.0 | 4.6 |
| Octanoic - Decanoic acids, Ethylene glycol diacetate | " | " | 4.0 | 4.4 |
| Octanoic - Decanoic acids, Isophorone | " | " | 4.1 | 4.9 |
| Octanoic - Decanoic acids, Methyl isoamyl ketone | " | " | 5.7 | 6.0 |
| Octanoic - Decanoic acids, Pelargonic acid | " | " | 4.7 | 4.7 |
| Octanoic - Decanoic acids, Acetophenone, Cinnamic acid | $(1/3)^3$ | $(2/5)^3$ | 5.0 | 4.9 |
| Octanoic - Decanoic acids, Decanoic acid, Isophorone | " | " | 4.0 | 4.0 |
| Pelargonic acid | 1 | 6.5 | 4.9 | 6.0 |
| Pelargonic acid, Butyl benzoate | $(1/2)^2$ | $(3/5)^2$ | 4.3 | 4.0 |
| Pelargonic acid, Dipropylene glycol dibenzoate | " | " | 5.3 | 5.6 |
| Pelargonic acid, Isophorone | " | " | 7.1 | 7.5 |
| Pelargonic acid, Methyl benzoate | " | " | 4.6 | 5.2 |
| Pelargonic acid, Methyl n-amyl ketone | " | " | 6.2 | 7.0 |
| Pelargonic acid, Methyl isoamyl ketone | " | " | 5.9 | 6.3 |
| Pelargonic acid, Methyl salicylate | " | " | 5.0 | 4.8 |
| Pelargonic acid, Neodecanoic acid | " | " | 5.4 | 5.9 |
| Pelargonic acid, Nitrobenzene | " | " | 5.3 | 5.3 |
| Pelargonic acid, Octanoic-Decanoic acids | " | " | 5.7 | 5.3 |
| Pelargonic acid, Sulfolane | " | " | 4.6 | 4.2 |
| Pelargonic acid, m-Toluic acid | " | " | 4.5 | 4.7 |
| Pelargonic acid, Acetophenone, Dipropylene dibenzoate | $(1/3)^3$ | $(2/5)^3$ | 4.0 | 4.8 |
| Pelargonic acid, Acetophenone, Glutaric acid | " | " | 4.0 | 4.2 |
| Pelargonic acid, Acetophenone, Methyl n-amyl ketone | " | " | 4.8 | 5.4 |
| Pelargonic acid, Acetophenone, Neodecanoic acid | " | " | 6.7 | 5.8 |
| Pelargonic acid, Acetophenone, Nitrobenzene | " | " | 4.2 | 8.3 |
| Pelargonic acid, Acetophenone, 3-Nitrotoluene | " | " | 6.7 | 9.3 |
| Pelargonic acid, Acetophenone, Octa-Deca acids | " | " | 6.0 | 5.5 |
| Pelargonic acid, Acetophenone, Sulfolane | " | " | 3.3 | 6.2 |
| Pelargonic acid, Benzoic acid, Isophorone | " | " | 5.0 | 3.5 |
| Pelargonic acid, Decanoic acid, Ethylene glycol diacetate | " | " | 4.7 | 4.3 |
| Pelargonic acid, Decanoic acid, Isophorone | " | " | 5.8 | 5.6 |
| Pelargonic acid, Dipropylene glycol dibenzoate, Ethylene glycol diacetate | " | " | 5.9 | 5.0 |
| Pelargonic acid, Dipropylene glycol dibenzoate, Isophorone | " | " | 4.3 | 3.7 |
| Pelargonic acid, Dipropylene glycol dibenzoate, Methyl n-amyl ketone | " | " | 4.0 | 4.1 |
| Pelargonic acid, Dipropylene glycol dibenzoate, Methyl benzoate | " | " | 4.1 | 4.2 |
| Pelargonic acid, Ethylene glycol diacetate, Methyl n-amyl ketone | " | " | 5.2 | 5.1 |
| Pelargonic acid, Ethylene glycol diacetate, Neodecanoic acid | " | " | 5.0 | 5.5 |
| Pelargonic acid, Ethylene glycol diacetate, Octa-Deca acids | " | " | 4.0 | 4.8 |
| Pelargonic acid, Neodecanoic acid, Methyl benzoate | " | " | 5.3 | 4.9 |
| Pelargonic acid, Neodecanoic acid, Methyl salicylate | " | " | 5.7 | 5.7 |
| Pelargonic acid, Methyl benzoate, Octa-Deca acids | " | " | 4.3 | 4.1 |
| Pelargonic acid, Methyl benzoate, Salicylic acid | " | " | 3.5 | 4.7 |
| Pelargonic acid, Octa-Deca acids, Methyl isoamyl ketone | " | " | 6.0 | 5.4 |
| Decanoic acid, Acetophenone | $(1/2)^2$ | $(3/5)^2$ | 5.0 | 3.9 |
| Decanoic acid, Benzyl benzoate | " | " | 4.2 | 5.9 |
| Decanoic acid, Cyclohexanone | " | " | 4.9 | 4.2 |
| Decanoic acid, Dipropylene glycol dibenzoate | " | " | 4.2 | 4.6 |
| Decanoic acid, Ethylene glycol diacetate | " | " | 5.4 | 4.0 |
| Decanoic acid, Isophorone | " | " | 5.5 | 6.2 |
| Decanoic acid, Neodecanoic acid, Benzyl benzoate | $(1/3)^3$ | $(2/5)^3$ | 4.7 | 5.3 |
| Decanoic acid, Neodecanoic acid, Isophorone | " | " | 3.1 | 4.9 |
| Decanoic acid, Dipropylene glycol dibenzoate, Ethylene glycol diacetate | " | " | 5.8 | 4.7 |
| Neodecanoic acid, Ethylene glycol diacetate | $(1/2)^2$ | $(3/5)^2$ | 4.0 | 4.2 |
| Neodecanoic acid, Isophorone | " | " | 4.1 | 4.5 |
| Neodecanoic acid, Nitrobenzene | " | " | 6.4 | 7.8 |
| Neodecanoic acid, Acetophenone, Nitrobenzene | $(1/3)^3$ | $(3/5)^3$ | 5.4 | 6.2 |
| Neodecanoic acid, Acetophenone, 3-Nitrotoluene | " | " | 6.0 | 5.0 |
| Neodecanoic acid, Methyl benzoate, 3-Nitrotoluene | " | " | 4.8 | 6.1 |

SUMMARY OF THE INVENTION

The objects of the invention are provided by a process for separating acetic acid from water which entails the use of mono carboxylic acids, either alone or admixed with certain oxygenated, nitrogenous and/or sulfur containing organic compounds.

DETAILED DESCRIPTION OF THE INVENTION

I have discovered that certain mono carboxylic acids, either alone or admixed with other organic compounds, will greatly improve the relative volatility of water to acetic acid and permit the separation of pure water from acetic acid by rectification when employed as the agent in extractive distillation. Table 1 lists the several acids and their mixtures and the approximate proportions that I have found to be effective. The data in Table 1 was obtained in a vapor-liquid equilibrium still. In each case, the starting material was an 80% acetic acid—20% water mixture. The ratios are the parts by weight of extractive agent used per part of acetic acid—water mixture. The relative volatilities are listed for each of the two ratios employed. Since the chromatograph is extremely sensitive to water, the relative volatilities listed are not normalized. They are peak height ratios. The concentration of acetic acid is actually much higher than indicated in Table 1 or in Examples 1, 2 and 3. Only in Example 4 is the data corrected to weight percentage of acetic acid.

The compounds which are effective when used alone are benzoic acid, hexanoic acid, heptanoic acid, octanoic acid and pelargonic acid. The compounds which are effective when used in mixtures are acetophenone, adiponitrile, butyl benzoate, dimethylformamide, N,N-dimethylacetamide, methyl salicylate, acetamide, cinnamic acid, salicyclic acid, benzophenone, decanoic acid, dipropylene glycol dibenzoate, ethylene glycol diacetate, isophorone, methyl n-amyl ketone, methyl benzoate, neodecanoic acid, nitrobenzene, 3-nitrotoluene, glutaric acid, methyl isoamyl ketone, benzyl benzoate, sulfolane, m-toluic acid and cyclohexanone.

The two relative volatilities shown in Table 1 correspond to the two different ratios employed. For example, in Table 1, one part of hexanoic acid with one part of the acetic acid—water mixture gives a relative volatility of 5.6. 6/5 parts of hexanoic acid give 6.5. One half part part of heptanoic acid mixed with one half part of isophorone with one part of the acetic acid—water mixture gives a relative volatility of 5.2, 3/5 parts of heptanoic acid plus 3/5 parts of isophorone give 6.4. One third part of neodecanoic acid plus ⅓ part of acetophenone plus ⅓ part of nitrobenzene with one part of the acetic acid—water mixture gives a relative volatility of 5.4, with 2/5 parts, these three give a relative volatility of 6.2. In every example in Table 1, the starting material is the 80% acetic acid—20% water mixture which possesses a relative volatility of 2.0

One of the compounds, pelargonic acid, listed in Table 1 and whose relative volatility had been determined in the vapor-liquid equilibrium still, was then evaluated in a glass perforated plate rectification column possessing 4.5 theoretical plates and the results listed in Example 4.

THE USEFULNESS OF THE INVENTION

The usefulness or utility of this invention can be demonstrated by referring to the data presented in Table 1. All of the successful extractive distillation agents show that acetic acid and water can be separated from each other by means of distillation in a rectification column and that the improvement in the ease of separation as measured by relative volatility is considerable. The data also show that the most attractive agents will operate at a boilup rate low enough to make this a useful and efficient method of recovering high purity acetic acid from any mixture with water. The stability of the compounds used and the boiling point difference is such that complete recovery and recycle is obtainable by a simple distillation and the amount required for make-up is small.

WORKING EXAMPLES

EXAMPLE 1

Fifty grams of the 80% acetic acid—20% water mixture and fifty grams of hexanoic acid were charged to an Othmer type glass vapor-liquid equilibrium still and refluxed for eleven hours. Analysis of the vapor and liquid by gas chromatography gave vapor composition of 87% water, 13% acetic acid and a liquid composition of 55.4% water, 44.6% acetic acid. This indicates a relative volatility of 5.4. Ten grams of hexanoic acid were added and refluxing continued for another thirteen hours. Analysis indicated a vapor composition of 87.6% water, 12.4% acetic acid; a liquid composition of 52.2% water, 47.8% acetic acid which is a relative volatility of 6.5.

EXAMPLE 2

Fifty grams of the acetic acid—water mixture, 25 grams of heptanoic acid and 25 grams of isophorone were charged to the vapor-liquid equilibrium still and refluxed for twelve hours. Analysis indicated a vapor composition of 79.6% water, 20.4% acetic acid; a liquid composition of 42.6% water, 57.4% acetic acid which is a relative volatility of 5.2. Five grams of heptanoic acid and five grams of isophorone were added and refluxing continued for another eleven hours. Analysis indicated a vapor composition of 80.6% water, 19.4% acetic acid; a liquid composition of 39.2% water, 60.8% acetic acid which is a relative volatility of 6.4.

EXAMPLE 3

Fifty grams of the acetic acid—water mixture, 17 grams of neodecanoic acid, 17 grams of acetophenone and 17 grams of nitrobenzene were charged to the vapor-liquid equilibrium still and refluxed for 16 hours. Analysis indicated a vapor composition of 86.2% water, 13.8% acetic acid; a liquid composition of 53.5% water, 46.5% acetic acid which is a relative volatility of 5.4. Three grams each of neodecanoic acid, acetophenone and nitrobenzene were added and refluxing continued for another twelve hours. Analysis indicated a vapor composition of 86.6% water, 13.4% acetic acid; a liquid composition of 51.1% water, 48.9% acetic acid which is a relative volatility of 6.2.

EXAMPLE 4

A glass perforated plate rectification column was calibrated with ethylbenzene and p-xylene which mixture possesses a relative volatility of 1.06 and found to have 4.5 theoretical plates. A solution comprising 380 grams of glacial acetic acid and 20 grams of water was placed in the stillpot and heated. When refluxing began, an extractive agent consisting of pure pelargonic acid was pumped into the column at a rate of 20 ml/min. The temperature of the extractive agent as it entered the column was 45° C. After establishing the feed rate of the extractive agent, the heat input to the acetic acid and water in the stillpot was adjusted to give a total reflux rate of 10–20 ml/min. After one hour of operation, the overhead and bottoms samples of approximately two ml. were collected and analysed using gas chromatography. The results were normalized and the overhed analysis was found to be 99.5% water, 0.5% acetic acid and the bottoms composition was 94% water, 0.6% acetic acid. This gave an average relative volatility of 5.92 for each theoretical plate using the Fenske equation for a 4.5 theoretical plate column. After 1½ hours of total operating time, the overhead and bottoms samples were again taken and analysed. The overhead composition was 99.5% water, 0.5% acetic acid and the bottoms composition was 93.8% water, 6.2% acetic acid. This gave an average relative volatility of 5.92 for each theoretical plate.

I claim:

1. A method for recovering acetic acid from a mixture of acetic acid and water which comprises distilling a mixture of acetic acid and water in a rectification column in the presence of about one to two parts of extractive agent per part of acetic acid—water mixture, recovering water as overhead product and obtaining the acetic acid and the extractive agent from the stillpot, the extractive agent comprises cinnamic acid and at least one material from the group consisting of acetophenone, adiponitrile, methyl salicylate and benzophenone.

* * * * *